United States Patent
Zhang et al.

(10) Patent No.: US 11,366,117 B2
(45) Date of Patent: Jun. 21, 2022

(54) APPLICATION OF EXOSOME TβRII PROTEIN AS A MARKER IN THE PREPARATION OF BREAST CANCER DETECTION KIT

(71) Applicant: ZHEJIANG UNIVERSITY, Hangzhou (CN)

(72) Inventors: Long Zhang, Hangzhou (CN); Feng Xie, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 218 days.

(21) Appl. No.: 16/632,101

(22) PCT Filed: Jun. 5, 2019

(86) PCT No.: PCT/CN2019/090046
§ 371 (c)(1),
(2) Date: Jan. 17, 2020

(87) PCT Pub. No.: WO2020/147252
PCT Pub. Date: Jul. 23, 2020

(65) Prior Publication Data
US 2021/0223247 A1    Jul. 22, 2021

(30) Foreign Application Priority Data
Jan. 14, 2019   (CN) .......................... 201910031748.0

(51) Int. Cl.
*G01N 33/574*       (2006.01)
*G01N 33/68*        (2006.01)

(52) U.S. Cl.
CPC . *G01N 33/57415* (2013.01); *G01N 33/57488* (2013.01); *G01N 33/6803* (2013.01)

(58) Field of Classification Search
CPC ....... G01N 33/57415; G01N 33/57488; G01N 33/6803
See application file for complete search history.

(56) References Cited

U.S. PATENT DOCUMENTS

2018/0010133 A1 *  1/2018  Li ...................... C12N 15/1138

FOREIGN PATENT DOCUMENTS

EP       1245676       10/2002

OTHER PUBLICATIONS

Lucia R. Languino et al., Exosome-mediated transfer from the tumor microenvironment increases TGF-beta signaling in squamous cell carcinoma, Am. J. Transl. Res., May 15, 2016, No. 5, vol. 8, pp. 2432-2437.
Clotilde Thery et al., Isolation and characterization of exosomes from cell culture supernanants and biological fluids, Current Protocols in Cell Biology, Apr. 1, 2006, No. 1, vol. 30, 3.22.1-3.22.29.

* cited by examiner

*Primary Examiner* — Misook Yu
*Assistant Examiner* — Dennis J Sullivan
(74) *Attorney, Agent, or Firm* — Jiwen Chen; Jacobson Holman PLLC

(57) ABSTRACT

The present invention discloses an application of the exosome TβRII protein as a marker in preparing a breast cancer diagnostic kit, and belongs to the technology field of breast cancer detection kits. The present invention finds that the content of TβRII positive exosomes in the serum of breast cancer patients is significantly higher than these of healthy people, and after the surgery, the content of TβRII exosomes in the serum of breast cancer patients reduces significantly, which suggests the value of the TβRII positive exosomes during the diagnosis and prognosis of breast cancer. The present invention provides a breast cancer diagnosis kit based on detecting exosome TβRII protein in peripheral blood, which is simple in operation, and only needs to extract a small amount of peripheral blood of the test population, thereby detecting whether the test population has breast cancer and evaluating the tumor of the patient. The degree of malignancy and the state of metastasis.

4 Claims, 5 Drawing Sheets

APPLICATION OF EXOSOME TβRII PROTEIN AS A MARKER IN THE PREPARATION OF BREAST CANCER DETECTION KIT

This is a U.S. national stage application of PCT Application No. PCT/CN2019/090046 under 35 U.S.C. 371, filed Jun. 5, 2019 in Chinese, claiming priority of Chinese Application No. 201910031748.0, filed Jan. 14, 2019, all of which are hereby incorporated by reference.

TECHNOLOGY FIELD

The present invention is related to the field of breast cancer detection kit and particularly related to an application of exosome TβRII protein as a marker in the preparation of breast cancer diagnostic kit.

BACKGROUND TECHNOLOGY

Breast cancer is the most common malignancy in women. It ranks second among the most common cancers worldwide. A prominent feature of breast cancer is its susceptibility to metastasis. The most common metastatic organ is bone, and 80% of patients who die because of bone metastases. Tumor metastasis is a very important cause of death in cancer patients, with up to 90% of solid tumor patients dying from tumor metastasis.

At present, there are two commonly used methods for detecting breast cancer metastasis. One is immunohistochemical technique, wherein pathological sections are prepared by collecting pathological tissues, and tumor metastasis is detected by detecting related proteins. The other method is Western blot, which has higher specificity. However, both of these methods require acquisition of tumor tissue. For some cancer patients who lack surgical indications or have contraindications for surgery, it is difficult to get the tissue for testing. Moreover, tumor metastasis is random, which increases the number of samples, making it more difficult to detect whether the metastasis happens.

Recent studies have found that exosomes play an important role in the occurrence, development and metastasis of cancer. Exosome is a special type of extracellular vesicles that are secreted by most cells and are generally 30-100 nm in diameter. They are microvesicles released from different cells into body fluids such as plasma, cerebrospinal fluid, urine or saliva. These transported substances closely relate to the pathogenesis of most human malignancies. Exosomes are released into the blood from tumor cells can provide cancer-related information and have a good prospect for non-invasive diagnosis of tumors.

According to a paper published on Nature by Kalluri on Jun. 24, 2015, a protein called Glypican-1 contained in exosomes derived from pancreatic cancer cells, may be suitable for non-invasive diagnosis and early pancreatic cancer screening during the treatment.

Breast cancer metastasis is a major cause of high mortality in breast cancer. Exosomes can reach the metastatic sites before the tumor cells, and can deeply intervene during metastasis. If specific antigens can be detected around the surface of the exosomes, this can help the researchers to give exact diagnosis and treatment to the patients. Specifically, if the specific antigen on the exosomes, which are secreted by breast cancer, can be obtained, the patient's disease state can be accurately determined and treated by accurate treatment.

Therefore, studying the active components contained in breast cancer exosomes and their molecular mechanisms and physiological significance in capturing target cells and affecting their functions has become a hot spot in cancer research, building a theoretical foundation for the development of new therapeutic drugs to cancers, such as breast cancer.

SUMMARY OF THE INVENTION

The object of the present invention is to provide a kit for detecting breast cancer, which can predict tumor occurrence and development by detecting peripheral blood, and overcome the difficulties that the breast cancer patients are not suitable for tissue specimens of breast cancer patients and the tumor malignancy and metastasis status are impossible to evaluate.

To achieve the above object, the present invention adopts the following technical solutions:

An application of exosomal TβRII protein as a marker in the preparation of a breast cancer detection kit.

Exosomes are extracellular vesicles that can be secreted from tumor cells into the peripheral blood circulation. The present study first publishes that the level of TβRII on the surface of exosomes in the serum of the breast cancer patients increases significantly. The transforming growth factor beta (TGF-β) signaling pathway plays a very important role in tumorigenesis and development. TGF-β inhibits tumor growth in early carcinogenesis, and transforms into a tumor promoting factor in the later stage of tumor development. During the later stage of breast cancer, TGF-β pathway is abnormally activated, leading to tumor metastasis. In the early stage of metastasis, it can be found that the exosome secreted by breast cancer cells contains a large amount of transforming growth factor beta receptor 2 (TGFBR2). Therefore, this indicator can be used as a marker for the diagnosis of breast cancer, especially for tumors that are difficult to diagnosis.

The present invention also provides a breast cancer detection kit based on detecting TβRII protein in peripheral blood exosomes, comprising a direct-labeled primary antibody against TβRII protein.

The kit provided by the present invention utilizes the specific binding of the primary antibody to the TβRII protein on the exosomes, and is able to make the qualitative or quantitative detection of the breast cancer marker TβRII protein by detecting the label on the direct standard primary antibody.

Preferably, the direct-labeled primary antibody is labeled with APC. Exosomes are incubated by APC-TβRII direct-labeled primary antibody, and the number of labeled exosomes can be detected by flow cytometry.

Specific procedures: loading samples, adjusting and determining the instrument's forward angular scattered light, side angle scattered light and FL1 basic parameters, FSC adopts Line linear form, SSC and FL1 adopt Log logarithm form, in FSC-H/SSC- The exosomes are circled on the H-scatter plot, and the excitation light is selected to be 633 nm. The fluorescence value of the exosomes is obtained in the FSC/APC scattergram, and more than 10,000 exosomes are read, and the scatter plot is analyzed.

The detection kit provided by the present invention comprises a reagent for pretreating peripheral blood, and the exosomes are separated and enriched.

Preferably, the breast cancer detecting kit further comprises a sodium citrate anticoagulant, wherein the sodium citrate has a mass percentage concentration of 2.5%.

Preferably, the breast cancer detecting kit further comprises a PBS buffer.

Preferably, the breast cancer detection kit further comprises a TβRII positive exosome standard of known concentration.

More preferably, the TβRII positive exosome standard is isolated from the breast cancer cell line MDA-MB-231 cell culture supernatant. The expression level of TβRII on the surface of exosomes secreted by MDA-MB-231 breast cancer cells is high, which can be used as a positive control for quantifying the number of TβRII positive exosomes in serum.

The present invention also provides a method of isolating exosomes in a blood sample, comprising the steps of:

(1) adding the sodium citrate anticoagulant to the collected peripheral blood samples, mixing well, centrifuging at 2000-4000 rpm for 10-20 min, and collecting the upper plasma;

(2) diluting the plasma with PBS buffer, ultracentrifuging at 100000-120000 g for 1-1.5 h, discarding the supernatant, and resuspending the pellet in PBS buffer, and ultracentrifuging at 100000-120000 g for 1-1.5 h. The precipitate is collected as the excretion body.

The use of nanosight and electron microscopy and known Marker (TSG101, CD63, Alix, etc.) detection of exosomes by immunoblotting have confirmed that the precipitated particles obtained from the peripheral blood samples of breast cancer patients by the above method contain breast cancer exosomes.

The present invention has these benefits:

The present invention finds that the number of TβRII positive exosomes in the serum of breast cancer patients is significantly larger than these of healthy people. And after the surgery, the level of TβRII exosomes in the serum of breast cancer patients reduces greatly, which suggests the value of the TβRII positive exosomes during the diagnosis and prognosis of breast cancer. Therefore, the content of TβRII protein in peripheral blood exosomes can be used as an indicator for breast cancer metastasis, and can also be used as a new target for tumor therapy. Exosome detection has the advantages, such as minimal-invasive, real-time detecting, etc. It can be used as a "liquid biopsy" for tumor development and metastasis. The breast cancer diagnostic kit based on the detection of serum TβRII in serum has a good application prospect in the diagnosis of breast cancer.

The detection kit provided by the invention has simple operation, and only needs to extract a small amount of peripheral blood of the test population, and can detect whether the test population has breast cancer, and is convenient and fast compared with the existing detection technology, and the influence of the test population is small. It does not use organic solvents such as phenol and chloroform, and has no toxic and side effects to operators. It is suitable for breast cancer prevention and detection in a large number of people.

THE DETAILED DESCRIPTION OF THE EMBODIMENTS OF THE INVENTION

In order to more fully understand the technical content of the present invention, the technical solution of the present invention will be further described below in conjunction with experiments.

Embodiment 1

1. Exaction and identification of exosome derived from human breast cancer cell line MDA-MB-231. The extraction method is as follows:

MDA-MB-231 cell culture supernatant was prepared, centrifuged at 4000 rpm/min for 10 min; the supernatant was collected and centrifuged at 100,000 g for 1 hour; the pellet was collected, and the pellet was resuspended in 28 ml of PBS buffer and centrifuged at 100,000 g for 1 hour. For exosomes. The exogenous body weight was suspended in 0.2 ml of PBS buffer and stored in −80° C. for use.

2. exosomes lysate lysis (composition: 2.5% SDS and 8 M urea, the balance is water) exosomes 30 minutes, determination of exosome concentration by BCA protein concentration; determination of isolated products by immunoblotting Tumor exosomes.

Figure 1:
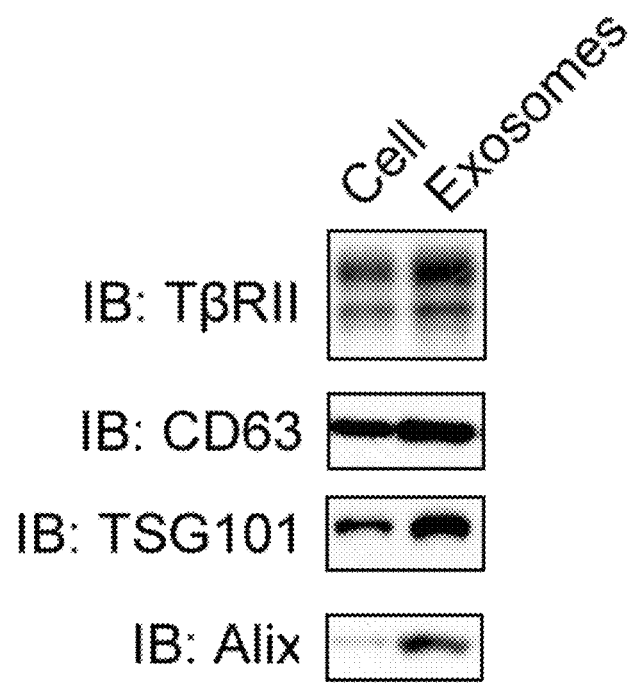
FIG. 1 shows the results of immunoblotting of human breast cancer cell MDA-MB-231 exosomes TβRII protein content.

As shown in FIG. 1, the isolated exosomes of step 1 contained a high protein content of TβRII in addition to the known markers TSG101, ALIX, and CD63.

3. Detection of exosomal TβRII by flow cytometry:

(1) APC-TβRII direct standard primary antibody (R&D Systems: Catalog #FAB241A) was added to the exosomes in a ratio of 1:100, and incubated for 30 minutes at room temperature in the dark, and washed three times with PBS;

(2) The average fluorescence intensity of TβRII in exosomes was determined by flow cytometry.

Model loading, adjusting and determining the instrument's forward angular scattered light, side angle scattered light and FL1 basic parameters, FSC adopts Line linear form, SSC and FL1 adopt Log logarithm form, and FSC-H/SSC-H scatter The exosomes were circled on the graph, and the excitation light was selected at 633 nm. The fluorescence value of the exosomes was obtained in the FSC/APC scattergram, and more than 10,000 exosomes were read, and the scattergram was analyzed.

Figure 2:
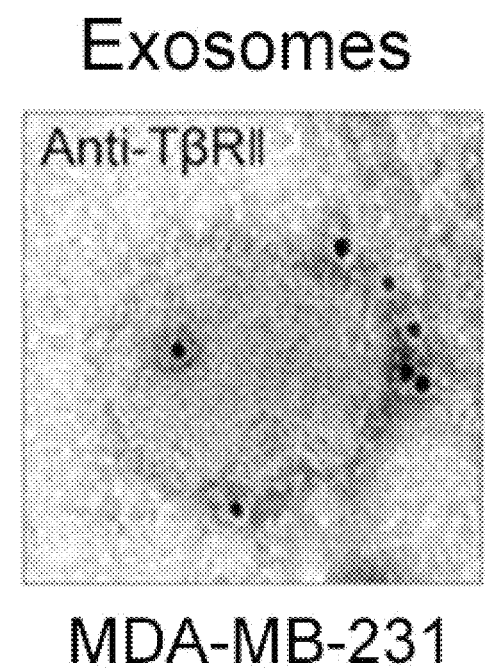
FIG. 2 shows the results of electron microscopy of TβRII protein content in human breast cancer cell MDA-MB-231 exosomes.
Figure 3:
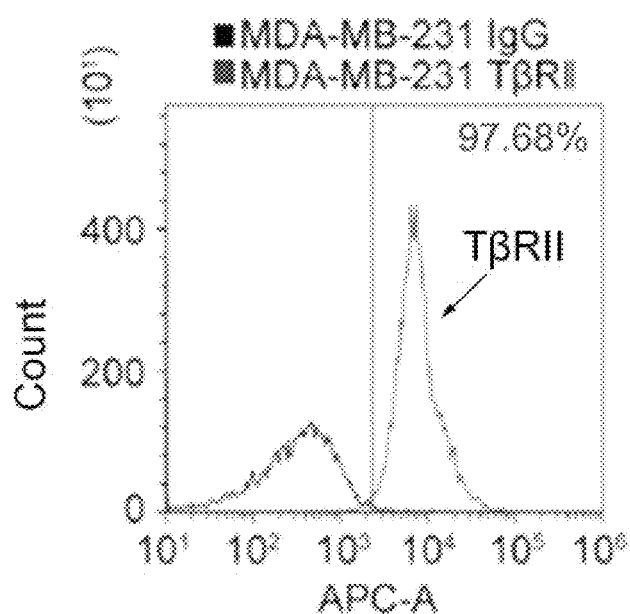
FIG. 3 shows the results of flow cytometry of human breast cancer cell MDA-MB-231 exosomes TβRII protein content.

4. The identification of MDA-MB-231 cell exosomes by electron microscopy showed that the prepared exosomes were small vesicles with a diameter of about 100 nm, with typical lipid bilayer structure and high TβRII content. (FIG. 2). The results of flow cytometry also showed that the content of TβRII in MDA-MB-231 cells was higher (FIG. 3).

Embodiment 2

Using the technique of Example 1, the peripheral blood exosomes of 36 breast cancer patients (20 normal samples were also tested as negative controls) were isolated and obtained and identified, and the expression of TβRII was detected.

1. Using ultracentrifugation to obtain exosomes in the peripheral blood of the population to be tested:

1 ml of venous blood from each sample was collected, 0.5 ml of 2.5% sodium citrate anticoagulant was added, mixed well, centrifuged at 4000 rpm/min for 10 min, and the upper layer of plasma was taken.

PBS was added to dilute the upper layer plasma to 28 ml, poured into an ultracentrifuge tube, and centrifuged at 100,000 g for 1 hour. The supernatant was discarded with a pipette or pipette, 1 ml of liquid was left at the bottom of the tube, PBS was added to 28 ml, the pellet was resuspended, and centrifuged at 100,000 g for 1 hour. The supernatant was discarded with a pipette or pipette, and the ultracentrifuge tube was put upside down on the filter paper for 5 min for thoroughly desorbing The liquid was resuspended by adding 0.5 ml PBS, transferred to a 1.5 ml centrifuge tube, and placed at −80° C. and preserved for research.

The exosomes were lysed by nanosight or exosome lysate for 30 minutes, and then the concentration was determined by BCA kit, and the morphology was observed by electron microscopy to confirm the isolation of tumor exosomes.

Figure 4:
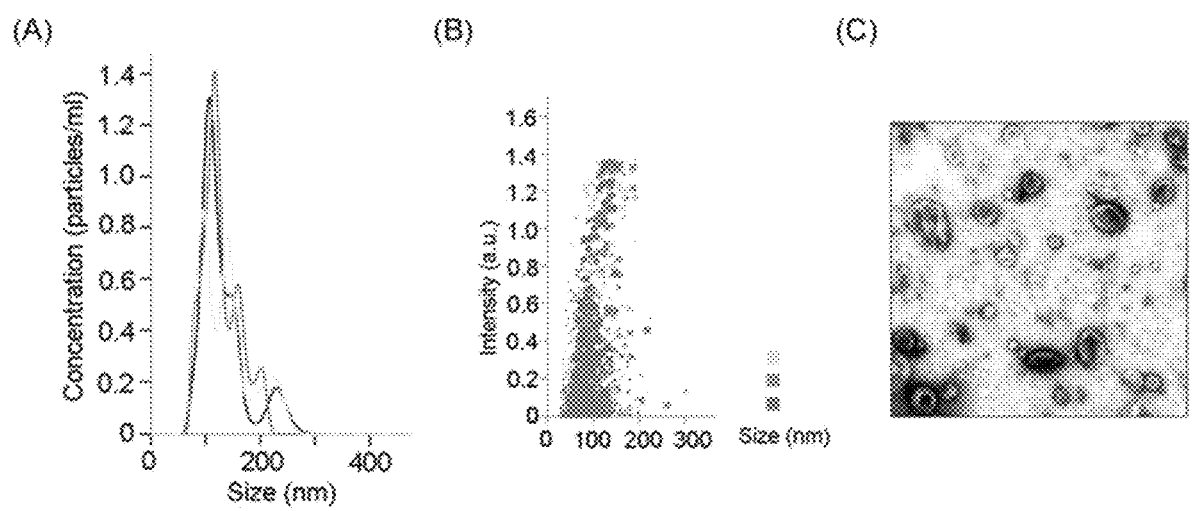
FIG. 4 is the diameter (A) of the isolated exosomes detected by nanosight, density (B) and the shape of the exosomes (C) taken by electron microscopy.

The results of the test: the particle diameter, density and other parameters detected by nanosight are consistent with the characteristics of the exosomes, and the particle size observed by electron microscopy is also consistent with the size of the exosomes. The isolated exosomes are obtained (FIG. 4).

Figure 5:
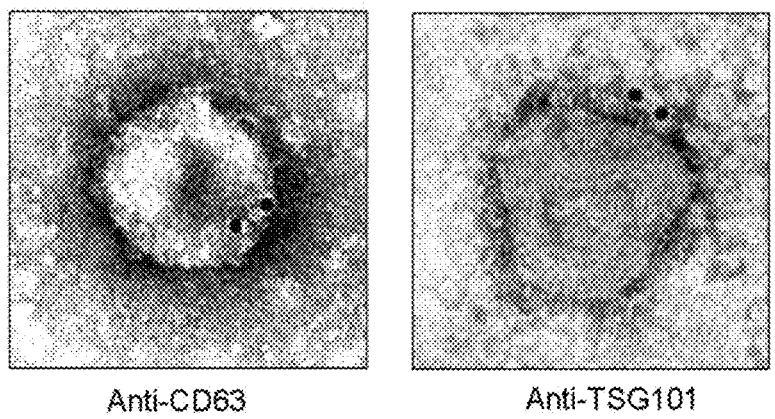
FIG. 5 is an exosome particle with an exosomal marker protein photographed with an electron microscope.

Further, the exosome-specific markers CD63 and TSG101 were detected by immunocolloidal gold electron microscopy. It was confirmed that these markers were present on the surface of the particles, and the exosomes were separated again (FIG. 5).

Second, the expression of TβRII on exosomes was detected by flow cytometry.

APC-TβRII direct-labeled primary antibody was added to the isolated exosomes in a ratio of 1:100, incubated for 30 minutes at room temperature in the dark, and washed three times with PBS.

The treated sample was tested for the content of TβRII in its exosomes by flow cytometry.

Figure 6:
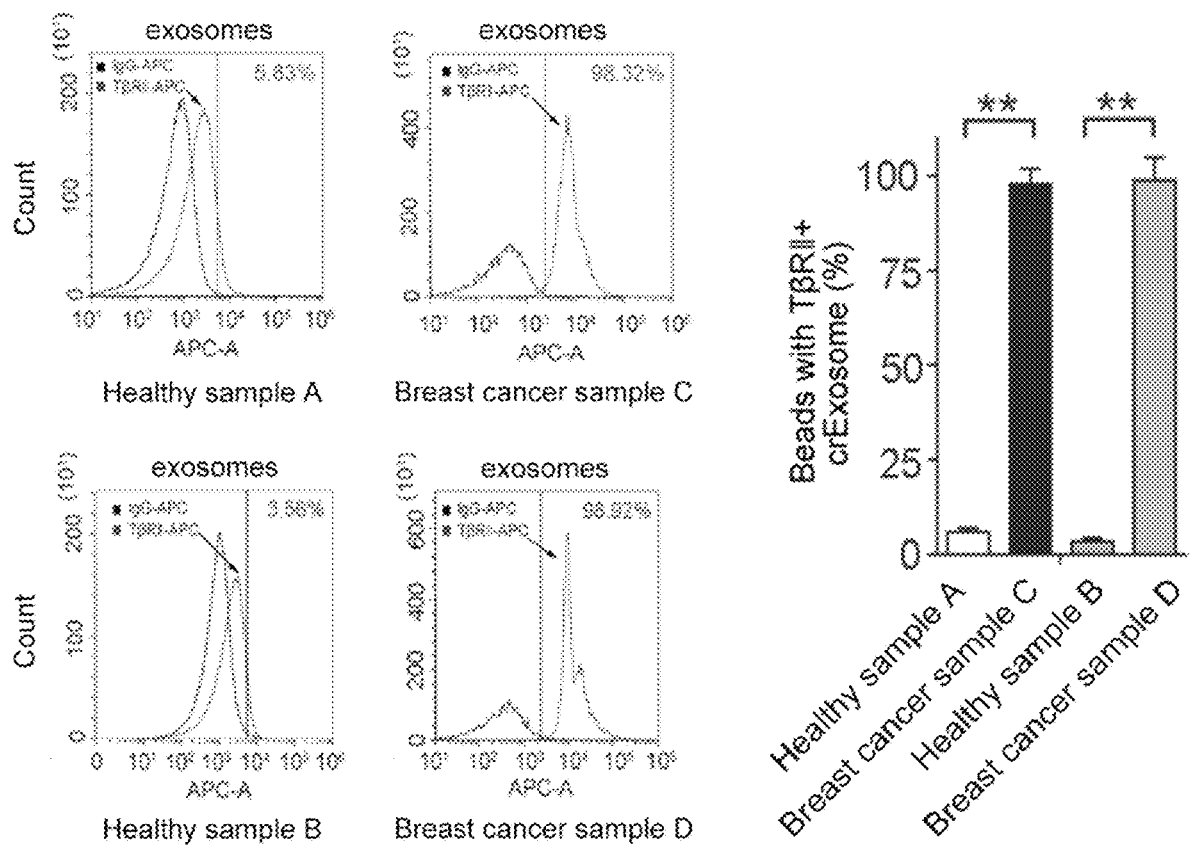
FIG. 6 shows the results of flow cytometry analysis of TβRII protein content in peripheral blood exosomes of breast cancer patients and normal subjects.
Figure 7:
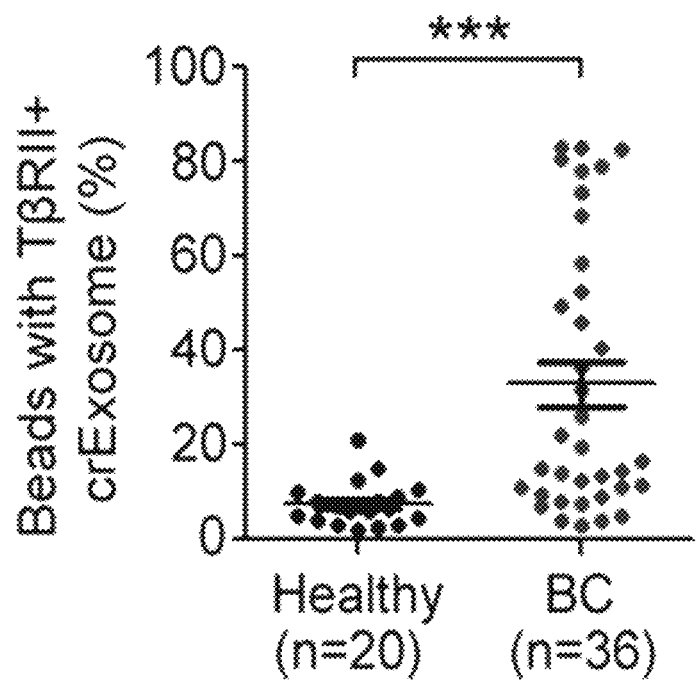
FIG. 7 is a graph showing the results of comparison of TβRII protein content in peripheral blood exosomes of breast cancer patients and normal subjects.

Test results: The content of TβRII in exosomes of breast cancer patients was higher than that in normal subjects (FIGS. 6, 7).

Figure 8:
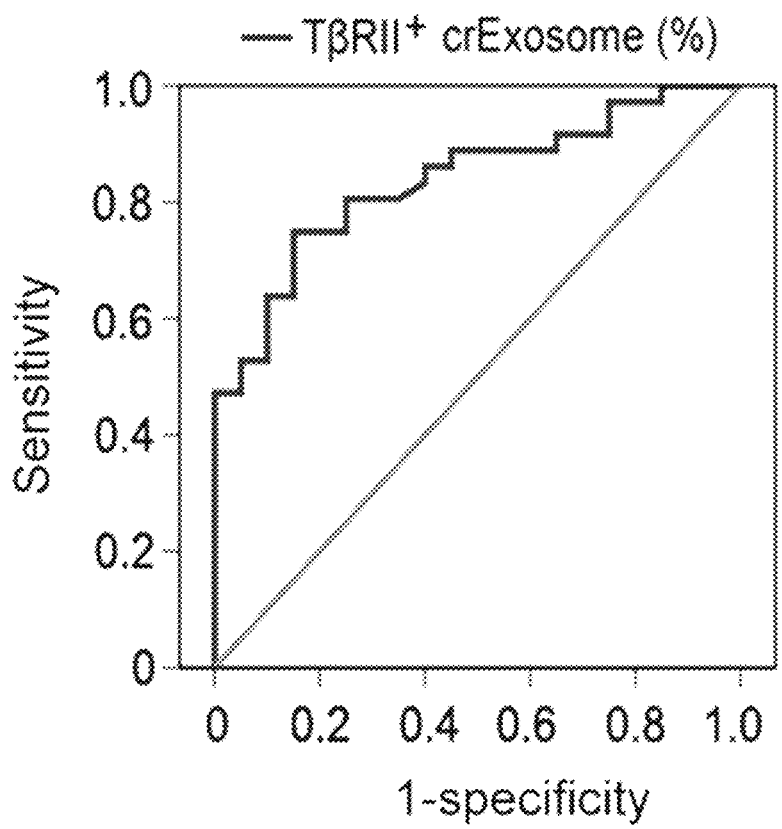
FIG. 8 is a graph showing the results of sensitivity and specificity analysis of peripheral blood exosomes TβRII protein in breast cancer patients and normal subjects.

Further analysis of the receiver's working curve showed that the peripheral blood exosome TβRII protein itself has a great advantage as a diagnostic marker for breast cancer, and its sensitivity and specificity are relatively high (FIG. 8).

Figure 9:
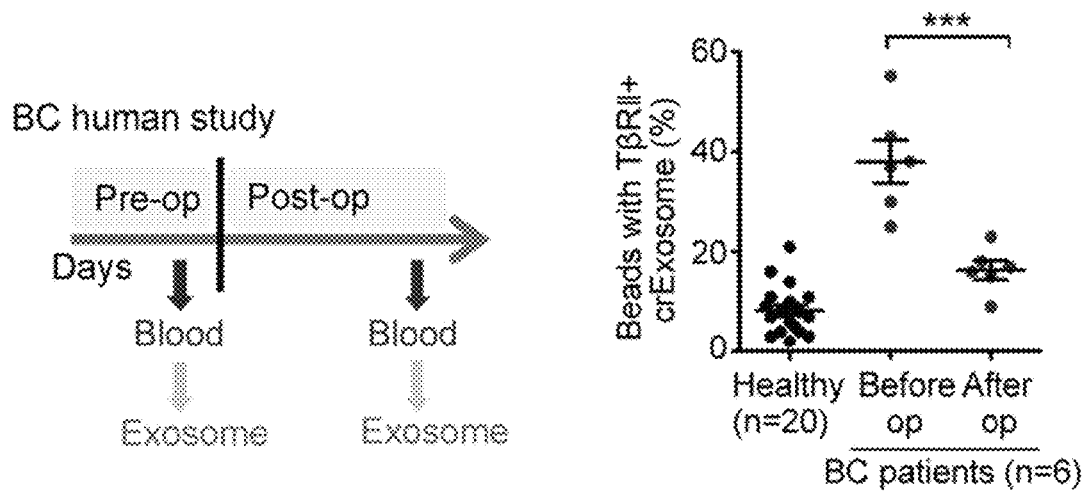
FIG. 9 is a schematic diagram showing the flow of peripheral blood exosomes from preoperative and postoperative patients (A) and the comparison of TβRII protein content in peripheral blood exosomes (B).
Figure 10:
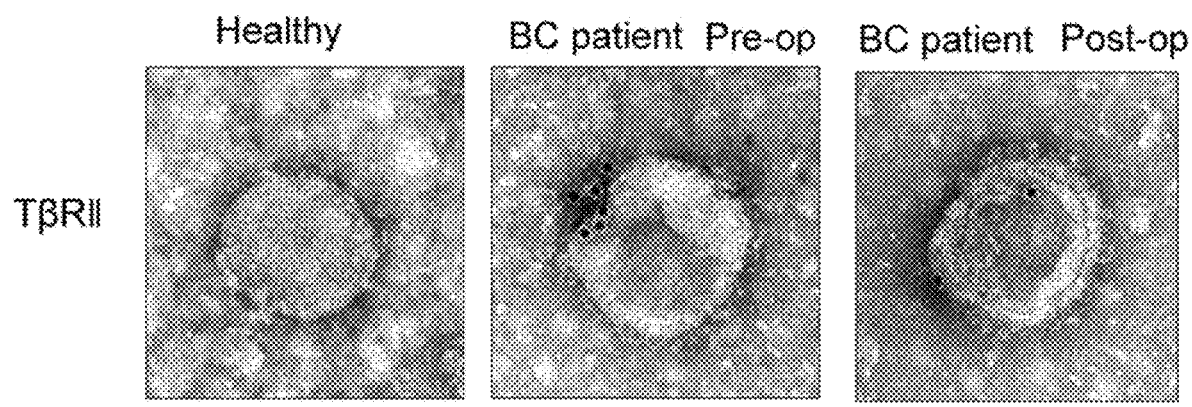
FIG. 10 shows the results of electron microscopy of TβRII protein in peripheral blood exosomes of patients with breast cancer before and after surgery.

Further analysis of TβRII protein content in peripheral blood exosomes of patients with breast cancer before and after surgery showed that the content of TβRII protein in peripheral blood exosomes of patients with breast cancer decreased significantly (FIG. 9) and detection by immunocolloid gold electron microscopy. The content of TβRII protein in exosomes of patients with breast cancer before and after surgery showed that the content of TβRII protein in peripheral blood exosomes of postoperative breast cancer patients also decreased significantly (FIG. 10). It indicates that the content of TβRII protein in peripheral blood exosomes can also be used as a test for postoperative rehabilitation of breast cancer patients.

The present invention collects serum of healthy people and breast cancer patients, and detects the content of TβRII positive exosomes by flow cytometry. Comparing the content of TβRII positive exosomes in healthy people and breast cancer patients, the best cut-off value was obtained, and the sensitivity and specificity of serum TβRII positive exosomes in breast cancer diagnosis were evaluated.

The serum levels of TβRII-positive exosomes in breast cancer patients were significantly higher than those in healthy people. It indicates the application prospect of detecting the content of TβRII positive exosomes in human serum in the diagnosis of breast cancer.

The invention claimed is:

1. A breast cancer detection kit based on the detection of TβRII protein in peripheral blood exosomes, which comprises a direct-labeled primary antibody against TβRII protein and a TβRII positive exosome standard, wherein the TβRII positive exosome standard is isolated from a breast cancer cell line MDA-MB-231 cell culture supernatant.

2. The breast cancer detection kit according to claim 1, wherein the direct-labeled primary antibody is marked with APC.

3. The breast cancer detection kit according to claim 1, wherein the breast cancer detection kit comprises a sodium citrate anticoagulant, and the sodium citrate has a mass percentage concentration of 2.5%.

4. The breast cancer detection kit according to claim 1, wherein the breast cancer detection kit comprises a PBS buffer.

* * * * *